United States Patent
Simpson et al.

(10) Patent No.: US 8,629,261 B2
(45) Date of Patent: Jan. 14, 2014

(54) OLIG1 MINI-PROMOTERS

(75) Inventors: Elizabeth M. Simpson, Vancouver (CA); Wyeth W. Wasserman, Vancouver (CA); Robert A. Holt, North Vancouver (CA); Steven J. Jones, Burnaby (CA); Daniel Goldowitz, Memphis, TN (US); Elodie Portales-Casamar, Vancouver (CA); Cletus D'Souza, Vancouver (CA); Vikramjit Chopra, Vancouver (CA)

(73) Assignee: The University of British Columbia (CA)

( * ) Notice: Subject to any disclaimer, the term of this patent is extended or adjusted under 35 U.S.C. 154(b) by 935 days.

(21) Appl. No.: 12/460,347

(22) Filed: Jul. 17, 2009

(65) Prior Publication Data

US 2010/0081201 A1    Apr. 1, 2010

Related U.S. Application Data

(60) Provisional application No. 61/129,785, filed on Jul. 18, 2008.

(51) Int. Cl.
*C07H 21/04* (2006.01)
*C12N 15/79* (2006.01)
*A61K 48/00* (2006.01)

(52) U.S. Cl.
USPC ............ 536/24.1; 435/320.1; 514/44 R

(58) Field of Classification Search
None
See application file for complete search history.

(56) References Cited

PUBLICATIONS

Lu, Q. et al., "Common Developmental Requirement for Olig function Indicates a Motor Neuron/Oligodendrocyte Connection", 2002, Cell, vol. 109: pp. 75-86.*
Gong, X. et al., "Olig1 is downregulated in oligodendrocyte progenitor cell differentiation", Aug. 2008, Neuroreport, vol. 19: pp. 1203-1207.*
Xie, W., et al., "Domains of the Rat rDNA Promoter Must be Aligned Stereospecifically", Mol.and Cell. Biol., 12(3): 1266-75.*
Bronson; et. al., "Single-copy transgenic mice with chosen-site integration", PNAS (1996), 93:9067-9072.
Clapcote; et al., "Simplex PCR assay for sex determination in mice", BioTechniques (2005), 38(5):702-706.
Hoagn-Xuan; et al., "OLIG-1 and 2 gene expression and oligodendroglial tumours", Neuropathology and Applied Neurobiology (2002), 28:89-94.
Jasin; et al., "Targeted transgenesis", PNAS (1996) 93:8804-8808.
Ligon; et al., "Olig Gene Function in CNS Development and Disease", GLIA (2006), 54:1-10.
Van Der Weyden; et al., "Tools for targeted manipulation of the mouse genome", Physiol Genomics (2002), 11:133-164.
Young; et al., "Fierce: a new mouse deletion of Nr2e1; violent behavious and ocular abnormalities are background-dependent", Behavioural Brain Research (2002), 132:145-158.

* cited by examiner

*Primary Examiner* — Michael Burkhart
(74) *Attorney, Agent, or Firm* — Bozicevic, Field & Francis LLP; Pamela J. Sherwood

(57) ABSTRACT

Isolated polynucleotides comprising an OLIG1 promoter are provided, where an OLIG1 regulatory element is operably joined to an OLIG1 basal promoter utilizing a non-native spacing between the promoter and regulatory elements. The promoter may be operably linked to an expressible sequence, e.g. reporter genes, genes encoding a polypeptide of interest, regulatory RNA sequences such as miRNA, siRNA, antisense RNA, etc., and the like. In some embodiments a cell comprising a stable integrant of an expression vector is provided, which may be integrated in the genome of the cell. The promoter may also be provided in a vector, for example in combination with an expressible sequence. The polynucleotides find use in a method of expressing a sequence of interest, e.g. for identifying or labeling cells, monitoring or tracking the expression of cells, etc.

Figure 1:
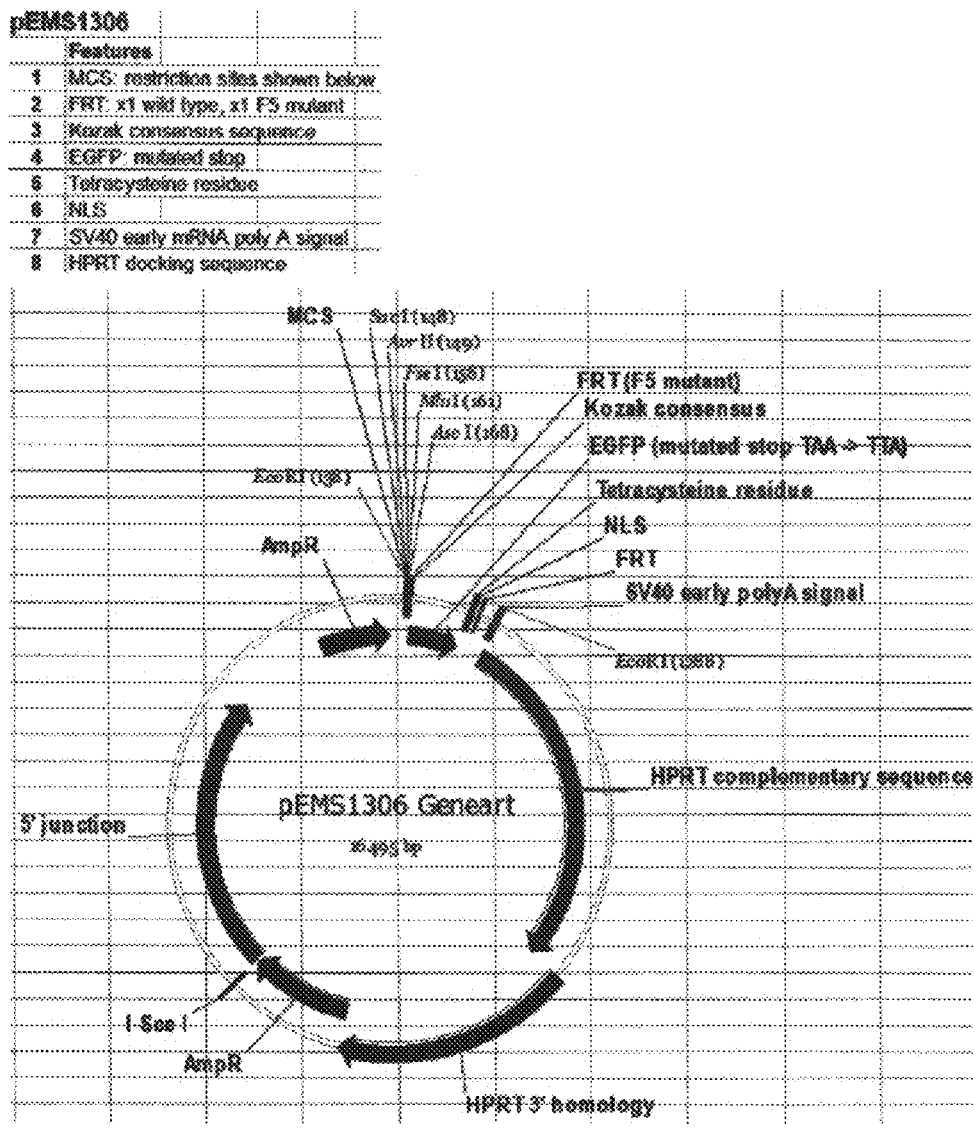

10 Claims, 4 Drawing Sheets
(3 of 4 Drawing Sheet(s) Filed in Color)

OLIG1 MINI-PROMOTERS

FIELD OF THE INVENTION

The invention relates to gene promoters and regulatory elements. More specifically, the invention relates to novel OLIG1 promoter compositions and related methods.

BACKGROUND

The Olig1 gene encodes a basic helix-loop-helix (bHLH) transcription factor, OLIG1 that along with the OLIG2 regulates key stages of early oligodendrocyte development. Myelinating oligodendrocytes fulfill diverse functional roles, such as ensheathment of neurons to facilitate electrical conductivity, maintenance of axonal integrity and participation in signaling networks with neurons. Olig1 gene function is critical for regulation of oligodendrogenesis during embryonic and fetal stages of CNS development, and it continues to be expressed in mature oligodendrocytes (Ligon et al. 2006). Elevated Olig1 expression has also been found in certain brain tumors, particularly oligodendrogliomas (Hoang-Xuan et al. 2002).

There exists a significant need for promoter elements which are capable of driving expression in specific cell types and/or in specific regions of the brain. Identification of minimal elements required for adequate expression and specificity will allow ease of use in expression constructs.

SUMMARY OF THE INVENTION

The present invention provides novel nucleic acid sequence compositions and methods, which relate to OLIG1 promoters having a sequence other than a native OLIG1 promoter.

In one embodiment of the invention, there is provided an isolated nucleic acid fragment comprising an OLIG1 mini-promoter, wherein the OLIG1 mini-promoter comprises one or more OLIG1 regulatory elements operably linked in a non-native conformation to an OLIG1 basal promoter. The OLIG1 promoter may have a nucleic acid sequence which is substantially similar in sequence and function to SEQ ID NO: 1. The one or more OLIG1 regulatory elements may have nucleic acid sequences which are substantially similar in sequence and function to SEQ ID NO: 2, SEQ ID NO: 3, and/or SEQ ID NO: 4. The OLIG1 basal promoter may have a nucleic acid sequence which is substantially similar in sequence and function to SEQ ID NO: 5. The OLIG1 promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule.

In one embodiment, there is provided an expression vector comprising an OLIG1 mini-promoter element, wherein the OLIG1 mini-promoter comprises one or more OLIG1 regulatory elements operably linked in a non-native conformation to an OLIG1 basal promoter. The OLIG1 promoter may have a nucleic acid sequence which is substantially similar in sequence and function to SEQ ID NO: 1. The one or more OLIG1 regulatory elements may have nucleic acid sequences which are substantially similar in sequence and function to SEQ ID NO: 2, SEQ ID NO: 3, and/or SEQ ID NO: 4. The OLIG1 basal promoter may have a nucleic acid sequence which is substantially similar in sequence and function to SEQ ID NO: 5. The OLIG1 promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may further comprise a genomic targeting sequence. The genomic targeting sequence may be HPRT.

In one embodiment, there is provided a method for selective expression of a gene, protein, RNA interference molecule or the like in a cell, the method comprising introducing into the cell a expression vector comprising an OLIG1 mini-promoter element of the invention, wherein the OLIG1 mini-promoter element comprises an OLIG1 regulatory element operably linked in a non-native conformation to an OLIG1 basal promoter element. Cells of interest include, without limitation, cells of the peripheral or central nervous system and progenitors thereof, e.g. embryonic stem cells, neural stem cells, neurons, glial cells, astrocytes, microglial cells, etc. The OLIG1 promoter may have a nucleic acid sequence which is substantially similar in sequence and function to SEQ ID NO: 1. The one or more OLIG1 regulatory elements may have nucleic acid sequences which are substantially similar in sequence and function to SEQ ID NO: 2, SEQ ID NO: 3, and/or SEQ ID NO: 4. The OLIG1 basal promoter may have a nucleic acid sequence which is substantially similar in sequence and function to SEQ ID NO: 5. The OLIG1 promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may thus further comprise a genomic targeting sequence. The genomic targeting sequence may be HPRT.

In one embodiment of the invention, there is provided a method for identifying or selectively labeling a cell, the method comprising introducing into the cell a expression vector comprising an OLIG1 mini-promoter element operably linked to an expressible sequence, wherein the OLIG1 mini-promoter element comprises one or more OLIG1 regulatory elements operably linked in a non-native conformation to an OLIG1 basal promoter element, and wherein the expressible sequence comprises a reporter gene. The OLIG1 promoter may have a nucleic acid sequence which is substantially similar in sequence and function to SEQ ID NO: 1. The one or more OLIG1 regulatory elements may have nucleic acid sequences which are substantially similar in sequence and function to SEQ ID NO: 2, SEQ ID NO: 3, and/or SEQ ID NO: 4. The OLIG1 basal promoter may have a nucleic acid sequence which is substantially similar in sequence and function to SEQ ID NO: 5. In some embodiments, the cell is a peripheral or central nervous system cell or progenitors thereof, including, without limitation, embryonic stem cells, neural stem cells, oligodendrocytes, glial cells, astrocytes, neurons and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, RNA interference molecule and the like.

In one embodiment of the invention, there is provided a method for monitoring or tracking the development or maturation of a cell, the method comprising: 1) introducing into the cell a expression vector comprising an OLIG1 mini-promoter element operably linked to an expressible sequence, wherein the OLIG1 mini-promoter element comprises one or more OLIG1 regulatory elements operably linked in a non-native conformation to an OLIG1 basal promoter element, and wherein the expressible sequence comprises a reporter gene; and 2) detecting the expression of the reporter gene in the progeny of the cell as a means of determining the lineage, identity or developmental state of the progenitor cell or progeny thereof. The OLIG1 promoter may have a nucleic acid sequence which is substantially similar in sequence and function to SEQ ID NO: 1. The one or more OLIG1 regulatory elements may have nucleic acid sequences which are substantially similar in sequence and function to SEQ ID NO: 2, SEQ ID NO: 3, and/or SEQ ID NO: 4. The OLIG1 basal promoter may have a nucleic acid sequence which is substantially similar in sequence and function to SEQ ID NO: 5. In some embodiments, the cell is a peripheral or central nervous system cell or progenitors thereof, including, without limitation, embryonic stem cells, neural stem cells, oligodendrocytes, glial cells, neurons and the like.

SHORT DESCRIPTION OF FIGURES

The patent or application file contains at least one drawing executed in color. Copies of this patent or patent application publication with color drawing(s) will be provided by the Office upon request and payment of the necessary fee.

FIG. 1. DNA expression vector (pEMS1306) into which OLIG1 promoter elements were inserted for expression studies. The OLIG1 promoter with a nucleic acid sequence corresponding to SEQ ID NO: 1 was inserted into the multiple cloning site (MCS) of the pEMS1302 vector such that it became operably linked to the enhanced green fluorescent protein (EGFP) reporter gene. The final construct, called OLIG1-D, also contained the HPRT genomic targeting sequence, an ampicillin resistance gene (AmpR) for screening, and a transcriptional termination sequence (SV40 polyA), as well as other elements necessary for vector replication and gene expression.

Figure 2:
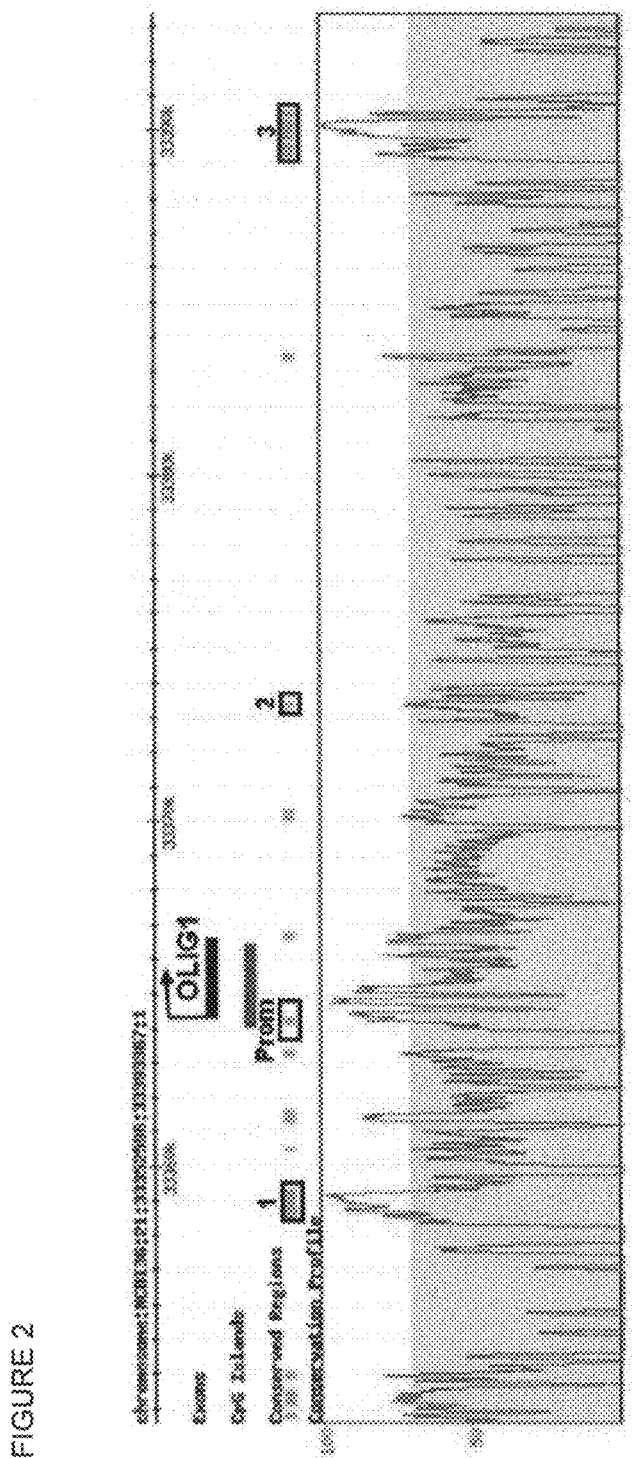

FIG. 2. From top to bottom, the human genomic sequence of OLIG1 located on chromosome 21 with an bent arrow indicating the transcription start site, the gene exon as a black box, the non-coding conserved regions as aqua boxes with open black boxes defining our candidate regulatory regions (basal promoter and regulatory elements), the conservation profile between the human and mouse sequences with the grey area delineating the 70% threshold used.

Figure 3:
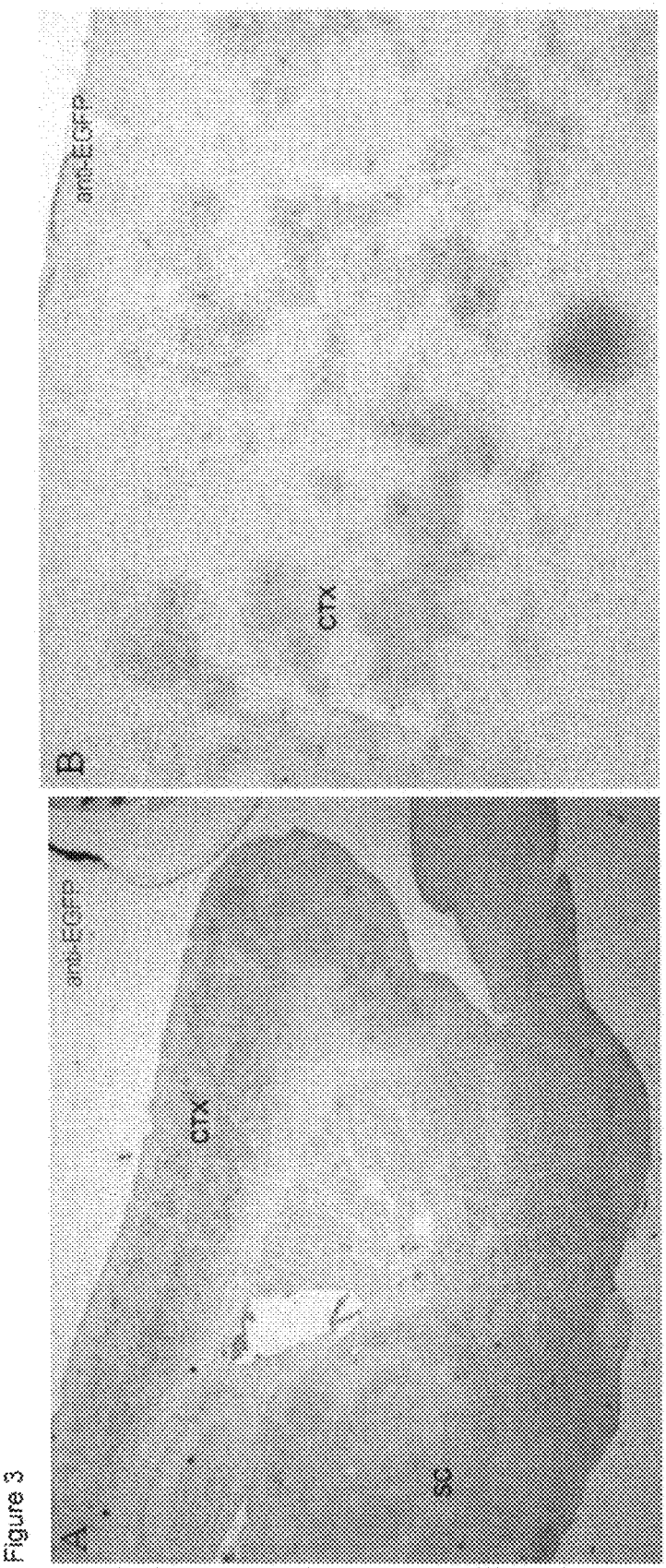

FIG. 3. EGFP expression is detected in multiple germline mice from the OLIG1-D mini-promoter strain in the initial anti-EGFP immunocytochemistry screen. Figures A and B illustrate the expression pattern throughout cortical (CTX) and subcortical (SC) regions following anti-GFP immunocytochemistry. Within the cortex, individual cell bodies are distinctly labelled and "puffy" processes surround these cells. The EGFP expression does not appear to be enriched in white matter tracts or in the corpus callosum.

Figure 4:
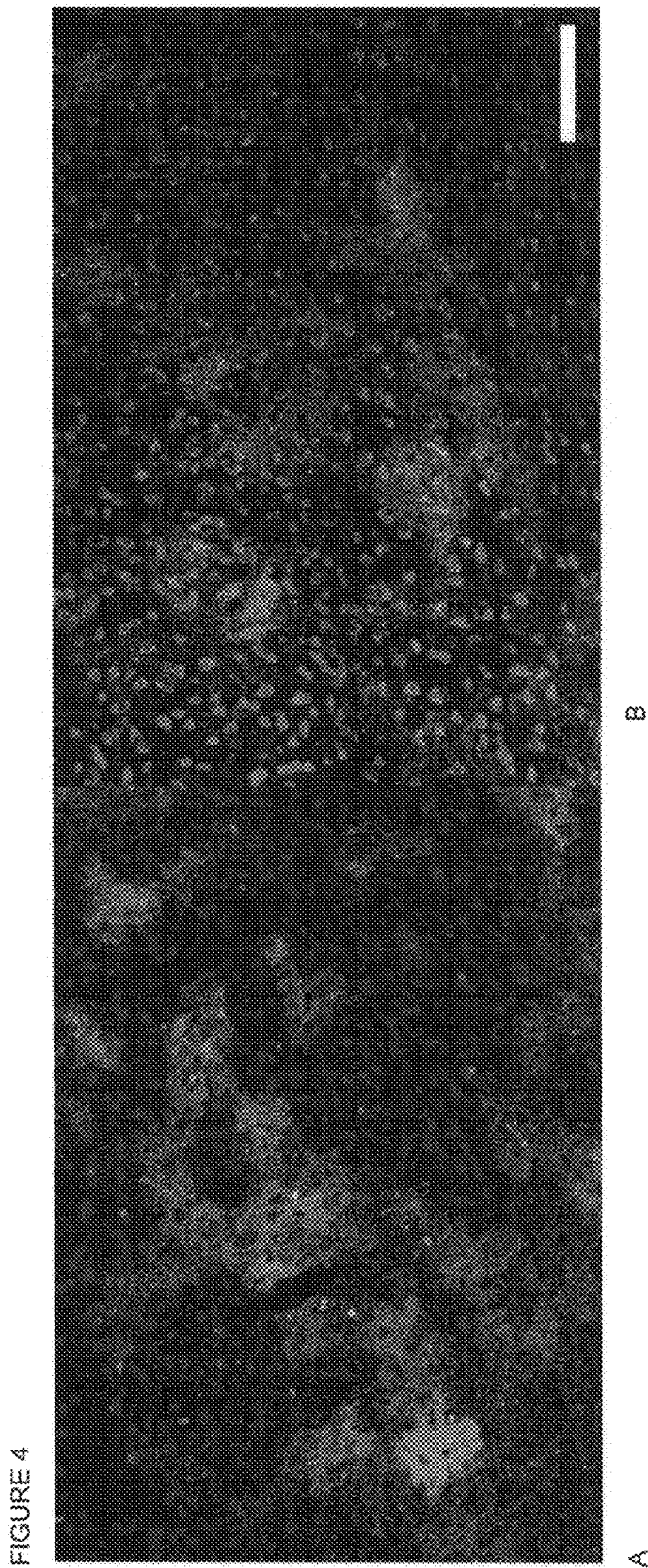

FIG. 4. Expression of reporter in oligodendrocytes by OLIG1-D promoter element. The OLIG1-D DNA expression vector was introduced into mouse embryonic stem cells (ESCs) at the HPRT locus. The ESCs were used to generate genetically modified mice containing OLIG1-D. Immunofluorescent analysis of mouse brain tissue sections revealed EGFP reporter expression in oligodendrocytes. Left—Anti-EGFP antibodies reveal diffuse staining (green) which partially overlaps with anti-olig2 staining for oligodendrocytes (red), and shows less staining in other cell types (blue, Toto3 nuclear stain). Right—Anti-EGFP antibodies reveal diffuse staining (green) which shows little overlap with neural specific (NeuN, red) staining and some overlap with general nuclear staining (blue, Toto3 nuclear stain).

DETAILED DESCRIPTION

The polynucleotide compositions of the present invention comprise a novel arrangement of OLIG1 promoter elements (also referred to herein as OLIG1 mini-promoters) as well as novel expression vectors comprising said arrangement of OLIG1 promoter elements (or mini-promoters). The present invention also includes various methods of utilizing these novel OLIG1 promoter (or mini-promoter) elements or expression vectors.

Provided is a sequence listing including certain of the OLIG1 mini-promoters, wherein SEQ ID NO:1 comprises the human OLIG1 mini-promoter (3042 bp). Nucleotides 1-1019 comprise the human OLIG1 regulatory element 1, which corresponds to SEQ ID NO: 2. Nucleotides 1020-1384 comprise the human OLIG1 regulatory element 2, which corresponds to SEQ ID NO: 3. Nucleotides 1385-2571 comprise the human OLIG1 regulatory element 3, which corresponds to SEQ ID NO: 4. Nucleotides 2572-3042 comprise the human OLIG1 basal promoter element, which corresponds to SEQ ID NO: 5.

The term 'OLIG1' refers to the gene that encodes the OLIG1 protein, and includes the controlling regulatory elements, e.g. promoters and the like. The term 'OLIG1' refers to the gene which encodes the OLIG1 protein, also referred to as oligodendrocyte transcription factor 1, oligodendrocyte-specific bHLH transcription factor 1, or BHLHB6. The human homolog of OLIG1 is encoded by the human gene identified as EntrezGene #116448 and is located at chromosomal location 21q22.11. The protein encoded by human OLIG1 has the Protein Accession Q8TAK6.2 (Swiss-Prot). Other mammalian OLIG1 homologs include but are not limited to: *Rattus norvegicus* (EntrezGene #60394, Protein Accession #Q9WUQ3.2), *Mus musculus* (EntrezGene #50914, Protein Accession #Q9JKN5.2).

The term 'promoter' refers to the regulatory DNA region which controls transcription or expression of a gene and which can be located adjacent to or overlapping a nucleotide or region of nucleotides at which RNA transcription is initiated. A promoter contains specific DNA sequences which bind protein factors, often referred to as transcription factors, which facilitate binding of RNA polymerase to the DNA leading to gene transcription. A 'basal promoter', also referred to as a 'core promoter', generally refers to a promoter that contains all the basic necessary elements to promote transcriptional expression of an operably linked polynucleotide. Eukaryotic basal promoters typically, though not necessarily, contain a TATA-box and/or a CAAT box. A 'OLIG1 basal promoter', in the context of the present invention and as used herein, is a nucleic acid compound having a sequence with at least 65%, at least 70%, at least 80%, at least 85%, at least 90%, at least 95%, or at least 99% similarity to SEQ ID NO: 5, and which comprises at least 1, usually at least 2, and may comprise all 3 of the identified conserved sequences listed in Table 1. The OLIG1 basal promoters of the present invention may comprise a TATA box such as that found in the native human OLIG1 promoter and/or a CAAT box such as that found in the native human OLIG1 promoter, and these elements should be positioned relative to the transcriptional start site (+1) in a way that is reflective of the native sequence.

TABLE 1

List of conserved sequences in the human OLIG1 basal promoter - SEQ ID NO: 5. The start and end coordinates of the sequences are relative to the full SEQ ID NO: 5 sequence. Conservation determined by alignment of 28 vertebrate species available through the UCSC genome browser

| Start (relative to SEQ ID NO: 5) | End (relative to SEQ ID NO: 5) | Invariant sequence type |
|---|---|---|
| 2838 | 2848 | Conserved sequence |
| 2911 | 2924 | Conserved sequence |
| 2980 | 2996 | Conserved sequence |

A promoter may also include one or more 'regulatory elements' which may also influence the expression or transcription by the promoter. Such regulatory elements encode specific DNA sequences which bind other factors, which may include but are not limited to enhancers, silencers, insulators, and/or boundary elements. An 'OLIG1 regulatory element', in the context of the present invention and as used herein, may be a nucleic acid compound having a sequence with at least 65%, at least 70%, at least 80%, at least 85%, at least 90%, at least 95%, or at least 99% similarity to SEQ ID NO: 2, and which comprises at least 4, usually at least 6, and may comprise all 7 of the identified conserved sequences listed in Table 2. An OLIG1 regulatory element may alternately be a nucleic acid compound having a sequence with at least 65%, at least 70%, at least 80%, at least 85%, at least 90%, at least 95%, or at least 99% similarity to SEQ ID NO: 3, and which comprises at least 1, usually at least 2, and may comprise all 3 of the identified conserved sequences listed in Table 3. An OLIG1 regulatory element may alternately be a nucleic acid compound having a sequence with at least 65%, at least 70%, at least 80%, at least 85%, at least 90%, at least 95%, or at least 99% similarity to SEQ ID NO: 4, and which comprises at least 3, usually at least 4, and may comprise all 5 of the identified conserved sequences listed in Table 4. The present invention provides, in certain embodiments as described herein, different promoters of the OLIG1 gene. In some embodiments, the OLIG1 promoter comprises one or more OLIG1 regulatory elements operably linked to a OLIG1 basal promoter. In certain embodiments, the OLIG1 regulatory elements are directly joined with no intervening sequences. In other embodiments, the OLIG1 regulatory elements may be operably linked with intervening sequences. In general the spacing between the regulatory elements is not more than about 15 KB, generally not more than about 10 KB, usually not more than about 1 KB, more often not more than about 500 nt, and may be not more than about 100 nt, down to a direct joining of the two sequences.

TABLE 2

List of conserved sequences in the human OLIG1 regulatory element 1: SEQ ID NO: 2. The start and end coordinates of the sequences are relative to the full SEQ ID NO: 2 sequence.

| Start (relative to SEQ ID NO: 2) | End (relative to SEQ ID NO: 2) | Invariant sequence type |
|---|---|---|
| 37 | 48 | Conserved sequence |
| 89 | 110 | Conserved sequence |
| 138 | 164 | Conserved sequence |
| 184 | 259 | Conserved sequence |
| 288 | 661 | Conserved sequence |
| 683 | 857 | Conserved sequence |
| 880 | 892 | Conserved sequence |

TABLE 3

List of conserved sequences in the human OLIG1 regulatory element 2: SEQ ID NO: 3. The start and end coordinates of the sequences are relative to the full SEQ ID NO: 3 sequence.

| Start (relative to SEQ ID NO: 3) | End (relative to SEQ ID NO: 3) | Invariant sequence type |
|---|---|---|
| 1052 | 1070 | Conserved sequence |
| 1143 | 1164 | Conserved sequence |
| 1189 | 1231 | Conserved sequence |

TABLE 4

List of conserved sequences in the human OLIG1 regulatory element 3: SEQ ID NO: 4. The start and end coordinates of the sequences are relative to the full SEQ ID NO: 4 sequence.

| Start (relative to SEQ ID NO: 4) | End (relative to SEQ ID NO: 4) | Invariant sequence type |
|---|---|---|
| 1622 | 1641 | Conserved sequence |
| 1695 | 2243 | Conserved sequence |
| 2299 | 2373 | Conserved sequence |
| 2384 | 2396 | Conserved sequence |
| 2420 | 2451 | Conserved sequence |

The term 'operably linked', in the context of the present invention, means joined in such a fashion as to work together to allow transcription. In some embodiments of the invention, two polynucleotide sequences may be operably linked by being directly linked via a nucleotide bond. In this fashion, the two operably linked elements contain no intervening sequences and in being joined are able to direct transcription of an expression sequence. In other embodiments of the invention, two elements may be operably linked by an intervening compound, for instance a polynucleotide sequence of variable length. In such a fashion, the operably linked elements, although not directly juxtaposed, are still able to direct transcription of an expression sequence. Thus, according to some embodiments of the invention, one or more promoter elements may be operably linked to each other, and additionally be operably linked to a downstream expression sequence, such that the linked promoter elements are able to direct expression of the downstream expression sequence.

The term 'mini-promoter' refers to a promoter in which certain promoter elements are combined in a non-native conformation, usually in such a fashion as to reduce the overall size of the promoter compared to the native conformation. For example, after identification of critical promoter elements, using one or more of various techniques, the native sequences that intervene the identified elements may be partially or completely removed. Other non-native sequences may optionally be inserted between the identified promoter elements. A mini-promoter may provide certain advantages over native promoter conformations. For example, the smaller size of the mini-promoter may allow easier genetic manipulation, ie. for the design and/or construction of expression vectors or other recombinant DNA constructs. In addition, the smaller size may allow easier insertion of DNA constructs into host cells and/or genomes, ie. via transfection, transformation, etc. Other advantages of mini-promoters would be apparent to one of skill in the art. In some embodiments of the invention, there are thus provided novel OLIG1 mini-promoters comprising one or more OLIG1 regulatory elements operably linked in a non-native conformation to an OLIG1 basal promoter. In general the spacing between the one or more OLIG1 regulatory elements and the OLIG1 basal promoter is not more than about 15 KB, generally not more than about 10 KB, usually not more than about 1 KB, more often not more than about 500 nt, and may be not more than about 100 nt, down to a direct joining of the two sequences.

The term 'expressible sequence' refers to a polynucleotide that is operably linked to a promoter element, such that the promoter element causes transcriptional expression of the expression sequence. An expressible sequence is typically linked downstream, on the 3'-end of the promoter element(s) in order to achieve transcriptional expression. The result of this transcriptional expression is the production of an RNA macromolecule. The expressed RNA molecule may encode a protein and may thus be subsequently translated by the appropriate cellular machinery to produce a polypeptide protein molecule. In some embodiments of the invention, the expression sequence may encode a reporter protein. Alternately, the RNA molecule may be an antisense, RNAi or other non-coding RNA molecule, which may be capable of modulating the expression of specific genes in a cell, as is known in the art.

The term 'RNA' as used in the present invention includes full-length RNA molecules, which may be coding or non-coding sequences, fragments, and derivatives thereof. For example, a full-length RNA may initially encompass up to about 20 Kb or more of sequence, and frequently will be processed by splicing to generate a small mature RNA. Fragments, RNAi, miRNA and anti-sense molecules may be smaller, usually at least about 18 nt. in length, at least about 20 nt in length, at least about 25 nt. in length, and may be up to about 50 nt. in length, up to about 100 nt in length, or more. RNA may be single stranded, double stranded, synthetic, isolated, partially isolated, essentially pure or recombinant. RNA compounds may be naturally occurring, or they may be altered such that they differ from naturally occurring RNA compounds. Alterations may include addition, deletion, substitution or modification of existing nucleotides. Such nucleotides may be either naturally occurring, or non-naturally occurring nucleotides. Alterations may also involve addition or insertion of non-nucleotide material, for instance at the end or ends of an existing RNA compound, or at a site that is internal to the RNA (ie. between two or more nucleotides).

The term 'nucleic acid' as used herein includes any nucleic acid, and may be a deoxyribonucleotide or ribonucleotide polymer in either single or double-stranded form. A 'polynucleotide' or 'nucleotide polymer' as used herein may include synthetic or mixed polymers of nucleic acids, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), and modified linkages (e.g., alpha anomeric polynucleotides, etc.). Also included are synthetic molecules that mimic polynucleotides in their ability to bind to a designated sequence via hydrogen bonding and other chemical interactions.

A 'purine' is a heterocyclic organic compound containing fused pyrimidine and imidazole rings, and acts as the parent compound for purine bases, adenine (A) and guanine (G). 'Nucleotides' are generally a purine (R) or pyrimidine (Y) base covalently linked to a pentose, usually ribose or deoxyribose, where the sugar carries one or more phosphate groups. Nucleic acids are generally a polymer of nucleotides joined by 3' 5' phosphodiester linkages. As used herein 'purine' is used to refer to the purine bases, A and G, and more broadly to include the nucleotide monomers, deoxyadenosine-5'-phosphate and deoxyguanosine-5'-phosphate, as components of a polynucleotide chain. A 'pyrimidine' is a single-ringed, organic base that forms nucleotide bases, such as cytosine (C), thymine (T) and uracil (U). As used herein 'pyrimidine' is used to refer to the pyrimidine bases, C, T and U, and more broadly to include the pyrimidine nucleotide monomers that along with purine nucleotides are the components of a polynucleotide chain.

It is within the capability of one of skill in the art to modify the sequence of a promoter nucleic acid, e.g. the provided basal promoter and regulatory sequences, in a manner that does not substantially change the activity of the promoter element, i.e. the transcription rate of an expressible sequence operably linked to a modified promoter sequence is at least about 65% the transcription rate of the original promoter, at least about 75% the transcription rate of the original promoter sequence, at least about 80%, at least about 90%, at least about 95%, at least about 99%, or more in a selected cell or suitable in vitro environment. Such modified sequences would be considered to be 'functionally similar' or to have 'functional similarity' or 'substantial functional similarity' to the unmodified sequence. Such modifications may include insertions, deletions which may be truncation of the sequence or internal deletions, or substitutions. The level of sequence modification to an original sequence will determine the 'sequence similarity' of the original and modified sequences. Modification of the promoter elements of the present invention in a fashion that does not significantly alter transcriptional activity, as described above would result in sequences with 'substantial sequence similarity' to the original sequence i.e. the modified sequence has a nucleic acid composition that is at least about 65% similar to the original promoter sequence, at least about 75% similar to the original promoter sequence, at least about 80%, at least about 90%, at least about 95%, at least about 99%, or more similar to the original promoter sequence. Thus, mini-promoter elements which have substantial functional and/or sequence similarity are herein described and are within the scope of the invention.

An 'RNA interference molecule', or 'RNA interference sequence' as defined herein, may include, but is not limited to, an antisense RNA molecule, a microRNA molecule or a short hairpin RNA (shRNA) molecule. Typically, RNA interference molecules are capable of target-specific modulation of gene expression and exert their effect either by mediating degradation of the mRNA products of the target gene, or by preventing protein translation from the mRNA of the target gene. The overall effect of interference with mRNA function is modulation of expression of the product of a target gene. This modulation can be measured in ways which are routine in the art, for example by Northern blot assay or reverse transcriptase PCR of mRNA expression, Western blot or ELISA assay of protein expression, immunoprecipitation assay of protein expression, etc.

An 'antisense RNA molecule', as used herein, is typically a single stranded RNA compound which binds to complementary RNA compounds, such as target mRNA molecules, and blocks translation from the complementary RNA compounds by sterically interfering with the normal translational machinery. Specific targeting of antisense RNA compounds to inhibit the expression of a desired gene may design the antisense RNA compound to have a homologous, complementary sequence to the desired gene. Perfect homology is not necessary for inhibition of expression. Design of gene specific antisense RNA compounds, including nucleotide sequence selection and additionally appropriate alterations, are known to one of skill in the art.

The term 'microRNA molecule', 'microRNA' or 'miRNA', as used herein, refers to single-stranded RNA molecules, typically of about 21-23 nucleotides in length, which are capable of modulating gene expression. Mature miRNA molecules are partially complementary to one or more messenger RNA (mRNA) molecules, and their main function is to down-regulate gene expression. Without being bound by theory, miRNAs are first transcribed as primary transcripts or pri-miRNA with a cap and poly-A tail and processed to short, 70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). When Dicer cleaves the pre-miRNA stem-loop, two complementary short RNA molecules are formed, but only one is integrated into the RISC complex. This strand is known as the guide strand and is selected by the argonaute protein, the catalytically active RNase in the RISC complex, on the basis of the stability of the 5' end. The remaining strand, known as the anti-guide or passenger strand, is degraded as a RISC complex substrate. After integration into the active RISC complex, miRNAs base pair with their complementary mRNA molecules and induce mRNA degradation by argonaute proteins, the catalytically active members of the RISC complex. Animal miRNAs are usually complementary to a site in the 3' UTR whereas plant miRNAs are usually complementary to coding regions of mRNAs.

The term 'short hairpin RNA' or 'shRNA' refers to RNA molecules having an RNA sequence that makes a tight hairpin turn that can be used to silence gene expression via RNA interference. The shRNA hairpin structure is cleaved by the cellular machinery into siRNA, which is then bound to the RNA-induced silencing complex (RISC). This complex binds to and cleaves mRNAs which match the siRNA that is bound to it. shRNA is transcribed by RNA Polymerase III whereas miRNA is transcribed by RNA Polymerase II. Techniques for designing target specific shRNA molecules are known in the art.

An 'expression vector' is typically a nucleic acid molecule which is may be integrating or autonomous, (i.e. self-replicating), and which contains the necessary components to achieve transcription of an expressible sequence in a target cell, when introduced into the target cell. Expression vectors may include plasmids, cosmids, phage, YAC, BAC, mini-chromosomes, viruses, e.g. retroviruses, adenovirus, lentivirus, SV-40, and the like; etc. Many such vectors have been described in the art and are suitable for use with the promoters of the present invention. Expression vectors of the present invention include a promoter as described herein, operably linked to an expressible sequence, which may also be optionally operably linked to a transcription termination sequence, such as a polyadenylation sequence. The expression vector optionally contains nucleic acid elements which confer host selectivity, elements that facilitate replication of the vector, elements that facilitate integration of the vector into the genome of the target cell, elements which confer properties, for example antibiotic resistance, to the target cell which allow selection or screening of transformed cells and the like. Techniques and methods for design and construction of expression vectors are well known in the art.

It may be desirable, when driving expression of an expressible sequence with a particular promoter system, to have the expression occur in a stable and consistent manner. A factor that has been shown to affect expression is the site of integration of an expression vector or construct into the genome of the target cell, sometimes called 'position effects'. Such position effects may be caused by, for example, local chromatin structure which affects expression of sequences from that region of the genome. One method to control for position effects when integrating an expression vector or construct into the genome of a target cell is to include a 'genomic targeting sequence' in the vector or construct that directs integration of the vector or construct to a specific genomic site. As an example, the hypoxanthine phosphoribosyltransferase (HPRT) gene has been used successfully for this purpose (Bronson et. al. 1996; Jasin et al. 1996). The HPRT gene has additional advantages as a genomic targeting sequence, for instance its concomitant use as a selectable marker system. Other genomic targeting sequences that may be useful in the present invention are described in the art, for instance (Jasin et al. 1996; van der Weyden et al. 2002). The genomic targeting signals as described herein are useful in certain embodiments of the present invention.

Introduction of nucleic acids or expression vectors may be accomplished using techniques well known in the art, for example microinjection, electroporation, particle bombardment, or chemical transformation, such as calcium-mediated transformation, as described for example in Maniatis et al. 1982, Molecular Cloning, A laboratory Manual, Cold Spring Harbor Laboratory or in Ausubel et al. 1994, Current protocols in molecular biology, Jolm Wiley and Sons.

OLIG1 Promoters

The present invention herein provides novel OLIG1 mini-promoter sequences which are capable of effecting transcriptional expression in a spatial and temporal fashion similar to naturally occurring OLIG1 promoters. The OLIG1 mini-promoters of the invention comprise OLIG1 promoter elements joined in a non-native configuration, thus providing advantageous characteristics. Also provided are novel expression vector compositions comprising OLIG1 mini-promoters which allow consistent specific spatiotemporal transcription of expression sequences. Also provided are novel methods utilizing these OLIG1 mini-promoters and expression vectors.

The OLIG1 promoters of the invention, as described herein, are referred to as 'mini-promoters' to reflect the fact that the mini-promoters comprise OLIG1 promoter elements that are joined in a non-native configuration. In this context, the native intervening sequences may have been partially or completely removed, and optionally may have been replaced with non-native sequences. In such a fashion, the natural spacing of the promoter elements, for instance the human OLIG1 regulatory elements corresponding to SEQ ID NO: 2, SEQ ID NO: 3 and/or SEQ ID NO: 4 and the human OLIG1 basal promoter element corresponding to SEQ ID NO: 5, or sequences with substantial functional and/or sequence equivalence, is altered. An advantage of such non-native mini-promoters is that the removal of native intervening sequences reduces the size of the mini-promoter while maintaining the functional activity of the promoter, thus improving the utility of the mini-promoter for various applications.

The inventors have demonstrated, as illustrated in the non-limiting Working Examples, that a human OLIG1 mini-promoter having a sequence corresponding to SEQ ID NO: 1, and which is comprised of directly linked human OLIG1 regulatory elements having a nucleic acid sequence corresponding to SEQ ID NO: 2, SEQ ID NO: 3 and SEQ ID NO:4 operably linked in a non-native conformation to a human OLIG1 basal promoter having a nucleic acid sequence corresponding to SEQ ID NO: 5, is capable of directing expression of an expressible sequence which is operably linked downstream of the OLIG1 promoter in specific cell types in different regions of the brain. The OLIG1 regulatory elements (SEQ ID NOs: 2, 3, 4) and OLIG1 basal promoter element (SEQ ID NO: 5) have sequences which are identical to those found upstream of the human OLIG1 gene, found on chromosome 21 of the human genome. To place these sequences in context, SEQ ID NO: 2 corresponds to absolute genomic coordinates chr21: 33358409-33359425 (strand +); SEQ ID NO: 3 corresponds to absolute genomic coordinates chr21:33373177-33373543 (strand +); SEQ ID NO: 4 corresponds to absolute genomic coordinates chr21: 33389511-33390692 (strand +); while SEQ ID NO: 5 corresponds to absolute genomic coordinates chr:21 33363932-33364402 (strand +), where the genomic coordinates are derived from NCBI Build 36.1 human genome assembly of March 2006. It is within the skill of one in the art to locate and determine these relative positions based on published sequence information for this gene, for instance found in the GenBank or PubMed public databases. It is understood that these genomic coordinates and relative positions are provided for the purposes of context, and that if any discrepancies exist between published sequences and the sequence listings provided herein, then the sequence listings shall prevail.

Promoters of the present invention may be modified with respect to the native regulatory and/or native basal promoter sequence. In general, such modifications will not change the functional activity of the promoter with respect to cell-type selectivity; and to the rate of transcription in cells where the promoter is active. The modified promoter provide for a transcription rate in a cell of interest of an expressible sequence operably linked to a modified promoter sequence that is at least about 75% the transcription rate of the promoter sequence of SEQ ID NO:1, at least about 80%, at least about 90%, at least about 95%, at least about 99%, or more. Methods of assessing promoter strength and selectivity are known in the art, including, for example, expression of a reporter sequence in a cell in vivo or in vitro, and quantitating the reporter activity.

Modifications of interest include deletion of terminal or internal regions, and substitution or insertion of residues. Applicants have identified 18 conserved sequences in the OLIG1 promoter (Table 5), where 12 such conserved sequences are present in the regulatory element, and 6 conserved sequences are present in the basal promoter. A promoter of interest in the present invention comprises generally at least 5, at least 10, usually at least 15, and may comprise all 18 of the identified conserved sequences, where the arrangement and spacing of conserved sequences may be the same as the native regulatory sequence, or may be altered, e.g. in the positioning and spacing of elements. Sequences set forth in SEQ ID NO:1 that are not conserved may be deleted or substituted, usually modifications that retain the spacing between conserved sequences is preferred. In general the spacing between each of the regulatory elements and between the regulatory elements and the basal promoter is not more than about 10 KB, generally not more than about 1 KB, usually not more than about 500 nt, and may be not more than about 100 nt, down to a direct joining of the two sequences.

TABLE 5

List of conserved sequences in SEQ ID NO: 1 (basal promoter + 3 regulatory elements). The start and end coordinates of the sequences are relative to the full SEQ ID NO: 1 sequence.

| Start (relative to SEQ ID NO: 1) | End (relative to SEQ ID NO: 1) | Invariant sequence type |
|---|---|---|
| 37 | 48 | Conserved sequence |
| 89 | 110 | Conserved sequence |
| 138 | 164 | Conserved sequence |
| 184 | 259 | Conserved sequence |
| 288 | 661 | Conserved sequence |
| 683 | 857 | Conserved sequence |
| 880 | 892 | Conserved sequence |
| 1052 | 1070 | Conserved sequence |
| 1143 | 1164 | Conserved sequence |
| 1189 | 1231 | Conserved sequence |
| 1622 | 1641 | Conserved sequence |
| 1695 | 2243 | Conserved sequence |
| 2299 | 2373 | Conserved sequence |
| 2384 | 2396 | Conserved sequence |
| 2420 | 2451 | Conserved sequence |
| 2838 | 2848 | Conserved sequence |
| 2911 | 2924 | Conserved sequence |
| 2980 | 2996 | Conserved sequence |

In some embodiments of the invention, there is thus provided an isolated nucleic acid fragment comprising an OLIG1 mini-promoter, wherein the OLIG1 promoter comprises an OLIG1 regulatory element operably linked in a non-native conformation to an OLIG1 basal promoter. In certain embodiments of the invention, the OLIG1 promoter may have a nucleic acid sequence which is substantially similar in sequence and function to SEQ ID NO: 1. The one or more OLIG1 regulatory elements may have nucleic acid sequences which are substantially similar in sequence and function to SEQ ID NO: 2, SEQ ID NO: 3, and/or SEQ ID NO: 4. The OLIG1 basal promoter may have a nucleic acid sequence which is substantially similar in sequence and function to SEQ ID NO: 5. The OLIG1 promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like.

It is an object of the present invention to provide means of expressing a gene, protein, RNA interference molecule or the like in a cell, tissue or organ. As such, the inventors thus provide novel expression vectors comprising OLIG1 mini-promoters which are capable of accomplishing this task. In some embodiments of the invention, there is provided a expression vector comprising an OLIG1 promoter element, wherein the OLIG1 promoter element comprises an OLIG1 regulatory element operably linked in a non-native conformation to an OLIG1 basal promoter element. The OLIG1 promoter element may have a nucleic acid sequence substantially similar in sequence and function to SEQ ID NO: 1. The OLIG1 regulatory element may have a nucleic acid sequence substantially similar in sequence and function to SEQ ID NO: 2. The OLIG1 basal promoter element may have a nucleic acid sequence substantially similar in sequence and function to SEQ ID NO: 3. The OLIG1 promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expression vector may further comprise a genomic targeting sequence. The genomic targeting sequence may be HPRT.

It is an object of the present invention to provide means of expressing a gene, protein, RNA interference molecule or the like in a cell, tissue or organ. As such, the inventors thus provide novel expression vectors comprising OLIG1 mini-promoters which are capable of accomplishing this task. In some embodiments of the invention, there is provided an expression vector comprising an OLIG1 promoter element, wherein the OLIG1 promoter element comprises one or more OLIG1 regulatory elements operably linked in a non-native conformation to an OLIG1 basal promoter element. The OLIG1 promoter element may have a nucleic acid sequence substantially similar in sequence and function to SEQ ID NO: 1. The one or more OLIG1 regulatory elements may have nucleic acid sequences which are substantially similar in sequence and function to SEQ ID NO: 2, SEQ ID NO: 3, and/or SEQ ID NO: 4. The OLIG1 basal promoter may have a nucleic acid sequence which is substantially similar in sequence and function to SEQ ID NO: 5. The OLIG1 promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expression vector may further comprise a genomic targeting sequence. The genomic targeting sequence may be HPRT.

The inventors have herein demonstrated that expression vectors comprising novel OLIG1 mini-promoter elements are capable of directing transcription of an expression sequence in specific cell types in specific regions of the brain, most notably the cortical and subcortical regions of the brain. In some embodiments of the invention, there is thus provided a method for expressing a gene, protein, RNA interference molecule or the like in the targeted cells of the brain. Cells of interest include, without limitation, cells of the peripheral or central nervous system and progenitors thereof, e.g. embryonic stem cells, neural stem cells, neurons, oligodendrocytes, glial cells, astrocytes, microgial cells, etc. The method comprises introducing into a cell or progenitor cell thereof an expression vector comprising an OLIG1 mini-promoter element, wherein the OLIG1 mini-promoter element comprises one or more OLIG1 regulatory elements operably linked in a non-native conformation to an OLIG1 basal promoter element. The OLIG1 promoter element may have a nucleic acid sequence substantially similar in sequence and function to SEQ ID NO: 1. The one or more OLIG1 regulatory elements may have nucleic acid sequences which are substantially similar in sequence and function to SEQ ID NO: 2, SEQ ID NO: 3, and/or SEQ ID NO: 4. The OLIG1 basal promoter may have a nucleic acid sequence which is substantially similar in sequence and function to SEQ ID NO: 5. The OLIG1 promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expression vector may thus further comprise a genomic targeting sequence. The genomic targeting sequence may be HPRT.

In other embodiments of the invention, there is provided a method for identifying or labeling a cell, the method comprising introducing into the cell a expression vector comprising an OLIG1 mini-promoter element operably linked to an expressible sequence, wherein the OLIG1 mini-promoter element comprises an OLIG1 regulatory element operably linked in a non-native conformation to an OLIG1 basal promoter element, and wherein the expressible sequence comprises a reporter gene. The OLIG1 promoter element may have a nucleic acid sequence substantially similar in sequence and function to SEQ ID NO: 1. The one or more OLIG1 regulatory elements may have nucleic acid sequences which are substantially similar in sequence and function to SEQ ID NO: 2, SEQ ID NO: 3, and/or SEQ ID NO: 4. The OLIG1 basal promoter may have a nucleic acid sequence which is substantially similar in sequence and function to SEQ ID NO: 5. The inventors have demonstrated that expression vectors comprising certain human OLIG1 promoter elements are capable of expression in specific regions of the brain, most notably the cortical and subcortical regions of the brain. In some embodiments, the cell is a peripheral or central nervous system cell or progenitors thereof, including, without limitation, embryonic stem cells, neural stem cells, oligodendrocytes, glial cell, neuronal cells, astrocytes, and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, RNA interference molecule and the like.

In further embodiments of the invention, there is provided a method for monitoring or tracking the development or maturation of a cell, including a cell of neural or oligodendrocyte lineage. The method comprises: 1) introducing into a progenitor to a cell, e.g. an embryonic stem cells, neural stem cell, neuronal progenitor cell, neuronal cell, oligodendrocyte progenitor cell, oligodendrocyte cell etc., an expression vector comprising an OLIG1 mini-promoter element operably linked to an expressible sequence, wherein the OLIG1 mini-promoter element comprises one or more OLIG1 regulatory elements operably linked in a non-native conformation to an OLIG1 basal promoter element, and wherein the expressible sequence comprises. a reporter gene; and 2) detecting the expression of the reporter gene in cell progeny of the cells as a means of determining the lineage, identity or developmental state of the cell or cell progeny. In such a fashion, one may be able to follow the development of a parent cell as it differentiates into more mature cells. As an example, one could introduce a expression vector comprising the aforementioned OLIG1 promoter elements into a pluripotent stem cell, monitor the expression of the reporter gene that is being expressed by the OLIG1 promoter elements during the maturation and differentiation of the stem cell and thus determine the state of maturation, for instance in the differentiation of the pluripotent stem cell into a mature cell. The inventors have demonstrated that the OLIG1 promoter elements described herein direct transcriptional expression in certain cell types, and so detection of reporter gene expression in a cell would thus be indicative of the cellular identity of the cell as being a particular type of cell.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

WORKING EXAMPLES

General Methods

Expression vector. The nucleic acid fragment corresponding to SEQ ID NO: 1 was inserted into the multiple cloning site of the pEMS1306 (see FIG. 1) to produce the expression vector OLIG1-D.

Derivation of mEMS1204 embryonic stem cells. Blastocysts were obtained from natural mating of B6-Hprt1$^{b-m3}$ females to 129-ROSA26 males at 3.5 dpc. Blastocysts were flushed from uterine horns as per (Hogan et al. 1994), cultured in EmbryoMax® KSOM with ½ Amino Acids, Glucose and Phenol Red (Cat #MR-121, Millipore/Chermicon, Temecula, Calif.) for 3-5 h, and then transferred onto mitomycin C (mitC; Cat#M4287, Sigma, Oakville, ON) mitotically inactivated B6-Hprt1$^{b-m3}$, B6129F1, or 129 mouse embryonic feeders (MEFs) derived from 13.5-day post-coital embryos (Ponchio et al. 2000) in 96-well plates containing KSR-ESC (Knockout™ D-MEM, Cat#10829-018, Invitrogen, Burlington, ON) with 2 mM L-glutamine (Cat#25030-081, Invitrogen, Burlington, ON), 0.1 mM MEM nonessential amino acid solution (Cat#11140-050, Invitrogen, Burlington, ON) and 16% Knockout™ Serum Replacement (Cat#10828-028, Invitrogen, Burlington, ON)) media (MEF media was replaced 3-5 hour prior to transfer).

Blastocysts were cultured as per (Cheng et al. 2004) with the following modifications: Cells were cultured for 7-9 days in KSR-ESC with minimal disturbance (checked on day 2 to determine if the blastocysts had 'hatched' out of the zona pellucida) and no media changes. Blastocysts which hatched and had a well developed ICM (inner cell mass) were treated with 20 µl 0.25% trypsin-EDTA (Invitrogen, Burlington, ON) for 5 min at 37° C., triturated with a 200 µl pipetman, inactivated with 30 µl 0.5 mg/ml soybean trypsin inhibitor (Invitrogen, Burlington, ON), and brought up to 200 µl with KSR-ESC, then transferred individually to a 24-well MEF plate containing 1800 µl KSR-ESC, for a total volume of 2 ml.

Beginning 4 days later, KSR-ESC media was replaced with FBS-ESC media (DMEM (Cat #11960-069, Invitrogen, Burlington, ON) with 2 mM L-glutamine (Invitrogen, Burlington, ON), 0.1 mM MEM nonessential amino acid solution (Invitrogen, Burlington, ON), 16% ES Cell Qualified fetal bovine serum (FBS, Invitrogen, Burlington, ON) and 0.01% β-mercaptoethanol (Sigma, Oakville, ON) in 25%, 50%, 75% proportions (respectively) to adapt the cells to FBS containing media.

On day 7 the cells were trypsinized to one well of a 24 well plate containing 1 ml of 100% FBS-ESC media, with daily media replacement. Once confluent, wells containing ESC colonies were expanded 3×24 wells (with MEFs), then passaged to 3×24 (with MEFs) and 3×12 well (plastic—no MEFs) for DNA analysis. Once confluent, the 3×24 wells were combined, aliquoted (3 vials), and frozen in ESC-freeze media (50% FBS, 40% FBS-ESC media, 10% DMSO (Sigma, Oakville, ON), and the 3×12 well treated with lysis buffer (Fisher Scientific, Ottawa, ON), mixed and aliquoted. Cultures were genotyped for X & Y chromosomes (Clapcote and Roder 2005), Gt(ROSA)26Sor$^{tm1Sor}$ and WT alleles and Hprt1$^{b-m3}$ and WT alleles. B6129F1-Gt(ROSA)26Sor$^{tm1Sor}$/+, Hprt1$^{b-m3}$/Y and B6129F1-Gt(ROSA)26Sor$^{tm1Sor}$+/+, Hprt1$^{b-m3}$/Y cell lines were identified.

Knock-in at the Hprt1 locus. The OLIG1-C plasmid DNA was purified with Qiagen Maxi Kit (Qiagen, Mississauga, ON), resuspended in 10:1 Tris-EDTA (TE, pH7.0) buffer, and linearized with I-Sce1 (New England Biolabs, Pickering, ON). Linearized plasmid DNA was resuspended in 85 µl of TE (10:0.1) to a final concentration of 187.5 ng/µl. mEMS1204 ESCs were grown to confluence on 4-6 T75 flasks of mitC treated Hprt1$^{b-m3}$ mouse embryonic feeders (MEFs) in FBS-ESC media. ESCs (1.7–2.5×10$^7$) in 720 µl 1×PBS were added to the linearized DNA and electroporated in a 4 mm electroporation cuvette (Bio-Rad Genepulser, Mississauga, ON), at 240 V, 50 µF, 6-10 msec pulse, immediately resuspended in a total volume of 5 ml of FBS-ESC media and plated onto 5×100 mm dishes of mitC B6129F1 MEFs in a total volume of 12 ml/100 mm dish. 24-36 h post-electroporation, correctly targeted homologous recombinants were selected for using HAT media (FBS-ESC media containing 1×HAT ((0.1 mM sodium hypoxanthine, 0.4 mM aminopterin, 0.16 mM thymidine), Cat#21060-017, Invitrogen, Burlington, ON). HAT media was changed every day for the first 3 days, and then every 3$^{rd}$ day thereafter, for up to 10 days. Individual colonies were counted and, typically, no more than 2 isolated colonies were picked per 100 mm dish to optimize for independent homologous recombination events. These colonies were expanded under standard protocols for verification of the desired recombination event.

Derivation of knock-in mice. Chimeric mice from untargeted and targeted ESCs were generated by microinjection (Hogan et al. 1994) into B6 (E14TG2a derived) and B6-Alb (E14TG2a and mEMS1204 derived) E3.5 blastocysts, or co-culture (Lee et al. 2007) with diploid ICR (Charles River, Wilmington Wash. Stock#022) E2.5 morula (cultured overnight to the blastocyst stage), followed by implantation into the uterine horns of 2.5 day pseudopregnant ICR females. Chimeras were identified and coat color chimerism determined as outlined below.

Male chimeras derived from the E14TG2a cell lines were mated with B6 or B6-Alb females, and germline transmission was identified in the former case by the transmission of the dominant A$^w$ (nonagouti; white bellied agouti) allele, making the progeny appear brown with a cream belly, or in the later case by the combination of A$^w$ and Tyr$^{c-ch}$ (tyrosinase; chinchilla), making the progeny appear golden. Non-germline progeny from the cross to B6 were homozygous for the recessive a (nonagouti; nonagouti) allele and appeared black, whereas non-germline progeny from the cross to B6-Alb were homozygous for the recessive Tyr$^c$ (tyrosinase; albino) allele and appeared white.

Male chimeras derived from the mEMS1204 cell lines were mated with B6-Alb females, and germline transmission identified by the presence of the dominant Tyr+ (tyrosinase; wild type) and the A$^w$ (nonagouti; white bellied agouti) or a (nonagouti; nonagouti) alleles making the progeny appear brown with a cream belly or black, respectively. Non-germline progeny were homozygous for the recessive Tyr$^{c-2J}$ (tyrosinase; albino 2 Jackson) allele and appear white. All germline female offspring should carry the knock-in X Chromosome and were mated with B6 males. N2 offspring were analyzed for the presence of the KI allele by PCR.

Determination of coat color chimerism. E14TG2a- and mEMS1204-derived chimeras were identified and level of coat color chimerism determined as follows. E14TG2a ESCs, homozygous for A$^w$ and Tyc$^{c-ch}$ as they are derived from the 129/OlaHsd strain (Hooper et al. 1987a; Hooper et al. 1987b), will produce chimeras with cream/chinchilla and agouti patches on a black background when injected into B6 blastocysts. The cream/chinchilla patches result from melanocytes derived solely from the ESCs (A$^w$/A$^w$, Tyr$^{c-ch}$/Tyr$^{c-ch}$), whereas agouti patches result from melanocytes that are a mixture of ESC (A$^w$/A$^w$, Tyr$^{c-ch}$/Tyr$^{c-ch}$) and host (a/a, Tyr$^c$/Tyr$^c$). However, E14TG2a ESCs, when injected into B6-Alb (a/a, Tyr$^c$/Tyr$^c$) produce chimeras with chinchilla and light chinchilla coat color patches on a white background. The former is derived solely from the ESCs (A$^w$/A$^w$, Tyr$^{c-ch}$/Tyr$^{c-ch}$), whereas the latter is again a mix of the ESC (A$^w$/A$^w$, Tyr$^{c-ch}$/Tyr$^{c-ch}$) and host (a/a, Tyr$^c$/Tyr$^c$). mEMS1204-derived chimeras were identified and coat color chimerism determined in the same manner.

mEMS1204 ESCs, heterozygous A$^w$/a and homozygous for the wild type Tyr+ alleles will produce chimeras with agouti and black patches on a white background when injected into B6-Alb blastocysts. The agouti patches result from melanocytes derived solely from the ESCs (A$^w$/a, Tyr+/Tyr+), whereas 'black' patches result from melanocytes that are a mixture of ESC (A$^w$/a, Tyr+/Tyr+) and host (a/a, Tyr$^{c-2J}$/Tyr$^{c-2J}$).

For E14TG2a injections into B6 and mEMS1204 injections into B6-Alb, overall chimerism was calculated by summing the percent of coat color patches derived solely from the ESC, plus half the percent of the ESC+host areas, where we conservatively estimated that half the melanocytes derive from the ESC and half from the host. For E14TG2a injections into B6-Alb, the similarity between chinchilla and light chinchilla on a white background presented difficulty when attempting to estimate overall coat color chimerism. As such, we estimated the percent chimerism based solely on the total chimerism observed when compared to a white mouse, resulting in slightly inflated overall percent chimerism for this small cohort of mice.

Immunohistochemistry and Immunofluorescence. Adult male chimeric and age matched control mice were perfused with 4% paraformaldehyde (PFA) as previously described (Young et al. 2002). Whole brains were dissected out and post-perfusion immersion fixed with PFA for 2-3 hours at 4° C. Brains were then transferred to 20% sucrose at 4° C. overnight with gentle shaking. The brains were cryostat sectioned sagittally at 12-14 μm and mounted on superfost-plus slides (Cat# 12-550-15, ThermoFisher Scientific, Waltham, Mass.). EGFP expression was detected by direct fluorescence of EGFP or by indirect immunofluorescence with anti-GFP antibodies (Abcam, Cambridge, Mass.) using a BioRad confocal laser scanning microscope (CLSM, BioRad, Hercules, Calif.).

For double label immunofluorescence analyses to determine cell types in the cerebellum, anti-GFAP was used in conjunction with direct EGFP fluorescence and imaged by CLSM (Liu et al. 2007). In brief, slide mounted brain sections, were permeabilized with phosphate buffered saline containing 0.1% triton-X100 (PBST), blocked with PBST containing 5% normal horse serum and 1% BSA, then incubated with primary antibodies overnight at room temperature in a humid chamber. Following three washes with PBST, the tissue were incubated with secondary antibodies (goat anti-rabbit-Alexa-594 conjugate, Molecular Probes, Eugene, Oreg.). The slides were counterstained with TOTO3/DAPI (1 μM each) for labeling all nuclei in confocal images. Bright field analyses were also conducted following immunocytochemical detection of anti-GFP using the Vectastain ABC kit and DAB as the chromogen to give a brown reaction product following the manufacturer's directions. Bright field images were visualized on a Zeiss Axiovert microscope and Axiovision Software (Carl Zeiss Microimaging, Thornwood, N.Y.).

Selection of OLIG1 promoter elements. Cross-species comparisons, or phylogenetic footprinting, were identified as a means to predict regulatory regions. The two mammalian species with the best evolutionary distance to use this approach are human and mouse. In the specific case of OLIG1, we computed the conservation level between human and mouse taking into consideration the non-coding sequence surrounding the OLIG1 gene. This genomic region including a lot of non-coding sequences conserved down to the frog, we set up a threshold of 70% of identity to select our candidate regulatory regions (FIG. 2). The OLIG1 basal promoter (SEQ ID NO: 5) and three regulatory regions (SEQ ID NOs: 2, 3, 4) were chosen based on these criteria.

Expression of reporter in glial cells by OLIG1-C promoter element. The OLIG1-D DNA expression vector comprising the OLIG1 promoter element corresponding to SEQ ID NO: 1 (which is itself comprised of SEQ ID NOs: 2, 3, 4 and 5) was introduced into mouse embryonic stem cells (ESCs) at the HPRT locus. The ESCs were used to generate genetically modified mice containing OLIG1-D. Immunohistochemical and immunofluorescence analysis of mouse brain tissue slices revealed EGFP expression throughout the cortical and subcortical regions of the brain, but not in the white matter or corpus callosum (FIG. 3). Expression was observed in oligodendrocytes (FIG. 4).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

REFERENCES

Bronson, S. K., E. G. Plaehn, et al. (1996). "Single-copy transgenic mice with chosen-site integration." *Proc Natl Acad Sci USA* 93(17): 9067-72.

Cheng, J., A. Dutra, et al. (2004). "Improved generation of C57BL/6J mouse embryonic stem cells in a defined serum-free media." *Genesis* 39(2): 100-4.

Clapcote, S. J. and J. C. Roder (2005). "Simplex PCR assay for sex determination in mice." *Biotechniques* 38(5): 702, 704, 706.

Hoang-Xuan, K., L. Aguirre-Cruz, et al. (2002). "OLIG-1 and 2 gene expression and oligodendroglial tumours." *Neuropathol Appl Neurobiol* 28(2): 89-94.

Hogan, B., R. Beddington, et al. (1994). *Manipulating the mouse*. Cold Spring Harbor, Cold Spring Harbor Laboratory Press.

Hooper, M., K. Hardy, et al. (1987a). "HPRT-deficient (Lesch-Nyhan) mouse embryos derived from germline colonization by cultured cells." *Nature* 326(6110): 292-5.

Hooper, M., K. Hardy, et al. (1987b). "HPRT-deficient (Lesch-Nyhan) mouse embryos derived from germline colonization by cultured cells." *Nature* 326: 292-295.

Jasin, M., M. E. Moynahan, et al. (1996). "Targeted transgenesis." *Proc Natl Acad Sci USA* 93(17): 8804-8.

Lee, K. H., C. K. Chuang, et al. (2007). "An alternative simple method for mass production of chimeric embryos by coculturing denuded embryos and embryonic stem cells in Eppendorf vials." *Theriogenology* 67(2): 228-37.

Ligon, K. L., S. P. Fancy, et al. (2006). "Olig gene function in CNS development and disease." *Glia* 54(1): 1-10.

Liu, L., E. E. Geisert, et al. (2007). "A transgenic mouse class-III beta tubulin reporter using yellow fluorescent protein." *Genesis* 45(9): 560-9.

Ponchio, L., L. Duma, et al. (2000). "Mitomycin C as an alternative to irradiation to inhibit the feeder layer growth in long-term culture assays." *Cytotherapy* 2(4): 281-6.

van der Weyden, L., D. J. Adams, et al. (2002). "Tools for targeted manipulation of the mouse genome."*Physiol Genomics* 11(3): 133-64.

Young, K. A., M. L. Berry, et al. (2002). "Fierce: a new mouse deletion of Nr2e1; violent behaviour and ocular abnormalities are background-dependent." *Behav Brain Res* 132(2): 145-58.

What is claimed is:

1. An isolated polynucleotide comprising OLIG1 regulatory elements, having at least 95% sequence identity to SEQ ID NO: 2, 3 and 4, wherein the sequence elements at SEQ ID NO: 2 residues 37-48; residues 89-110; residues 138-164; residues 184-259; residues 288-661; residues 683-857; residues 880-892 are conserved and present in said polynucleotide; the sequence elements at SEQ ID NO:3, residues 33-51; residues 124-145; residues 170-212 are conserved and present in said polynucleotide; the sequence elements at SEQ ID NO:4 residues 238-257; residues 311-859; residues 916-989; residues 1000-1012; residues 1037-1067 are conserved and present in said polynucleotide;

operably joined to an OLIG1 basal promoter having at least 95% sequence identity to SEQ ID NO:5 wherein the sequence elements at SEQ ID NO:5, residues 267-277; residues 340-353; and residues 409-426 are conserved and present in said polynucleotide, through a non-native spacing of not more than 1 kb between the promoter and the regulatory elements.

2. An isolated polynucleotide having at least 95% sequence identity to SEQ ID NO:1.

3. The isolated polypeptide of claim 1, wherein the polynucleotide comprises the sequence set forth in SEQ ID NO:1.

4. The isolated polynucleotide of claim 1, operably linked to an expressible sequence.

5. A vector comprising the isolated polynucleotide of claim 1.

6. A vector comprising the isolated polynucleotide of claim 4.

7. A cell comprising the vector of claim 6.

8. The cell of claim 7, wherein the vector is stably integrated into the genome of the cell.

9. The cell of claim 8, wherein the cell is a stem cell.

10. A method of expressing a sequence of interest, the method comprising operably linking the sequence of interest to the polynucleotide of claim 1; and introducing into a cell permissive for expression from the OLIG1 promoter.

* * * * *

SEQUENCE LISTING

```
<160> NUMBER OF SEQ ID NOS: 5

<210> SEQ ID NO 1
<211> LENGTH: 3042
<212> TYPE: DNA
<213> ORGANISM: Homo sapiens

<400> SEQUENCE: 1
tgttcaactc ggatagtcct caccactgag ttaatatttc caggtcagag cgcctccgag      60
agaaaaaggc ggtggccttg gagctctggt ctccttaact gcaccctggg aagtcttcac     120
acggcctttc ttccccctggt ggtctaatct ggagtcagat ccagccgtca gctcttacag    180
acggggaagg accgggagcc aacgggaaaa caacaggtga gcttgtgaac aagtcccctt     240
ctgtgtctcg ggcagggtgt ctgccgggc aaccgtgggg ctgcactgac ttccagaacc      300
ttctgcctct gcaggtgttt taggaacttg gcctcagcgc ttcagtgacc catatttat     360 tacctttcag gtttctataa ttcatcattc actcctttct gaaaacctag aatgaaaaag     420
tttagcagct cagcgccgcg gcctctctcc attctctccc caaacacatc ggcctgtttg     480
ttctctttca tccccgctct tcctgttgca ttctgccggt tcaatgggga aggagtgaaa     540
ccggatggct ggacccagtg cggggaaatg acttcagagc caccttttgtt tccctcattc    600 cttgagcgc acttggccct gcgtctctat gaaagggctt gttgaacca ttcggaacat      660 ccagcaagcc agagatgctg cggccagaac cgctcgcatc ttttcaggct gcctgagact    720
ctgggttaaa ctgccaaatt tttgcaacaa aactaaccat gacattggac attgtgttat    780
aaattagcca cagccttcca agcaaattgt ctctttttat tgtatcagtg taagcctcgg    840
aaacatttgg cttcagctac taccttcagg gaggctcaga ggatattttt gttctgcccc    900
aaaccaactc ttcagacacc gagttgcatg tgctaatacc catatcttca ttcacagtta    960
ttcttatcac actccctctg agaacctctg tcagttatgt tctatttctc tgcctcccag   1020
aaccttcctt gtcctcacgc ttgactagca gacaatgggt tcttcagaag ccacagcatt  1080
tcagctgttt tggccccaga ggccacaagc tgactgcatg tcattctcca ccagcagagc  1140
gtcacctcgg ggtagctcca aacagtatca accggtttgt ggtgagtgga taaacaccag  1200
gctgggtgaa tgaagtcaca ggctgagtca tcctctgcac atgggggctg aatgggctc    1260 agtcaggccc agaggagcct ccccggcaag gtgctggggg ccaggctctc cctgccagtg  1320
aggctggggt ccgtccccaa tagtcattcc tttggccaac aaacacttat tgagcgccca  1380
```

```
cctagctctt caagtcgcag ataacagtga aggccctaag actcaccatc caaaacagtt    1440
ttggaaaaaa accaaagaag agaaaataat ttcaaacctt aaagcaatgc atggtgattc    1500 tctgggggt ctaagaattt ctcccagaga aatgataagg cagacaaatg gaagatcaat    1560
gaagcaacat cgtggcaata atgcaattgg tcctgccgta gtcatgaaca tgtaaataac    1620
aagacagcaa taagaagacc ccagactctg cctagaaaca aaatattcag cctgttgttg    1680
ttgtttctta ttgcaggatt ttgagtgaaa agtagttcc acttgtcaat cagctacgtt    1740 gcagggcta atagattctg tgtgttaggg aggtcaacac ggaatttaat ttaacatctc    1800
acaatacacc cacatgccca gaaaatgtgg acagcttgat agggttcact gagccaaaga    1860
agcaagaccc aaacagtgca ttaatgtata ggggaagaat agttgcaatc agccccttgt    1920
gaattggaca gagggcttgg agatgaagca attatcagcc atcggggatt aatagtaaag    1980
tgtgaatacc aagctgtata tgttaggggc agaatatgtt gcctatagaa aacaacaaag    2040
gacgtttctt actattaagt gagattaaac gtaatggcct gatttaatca caaaggcaga    2100
attaaattca gatggcaact tcaaagtgga cacaggaaca caggccactg cttacattta    2160
catatagctg gcatagcttg gcctgcaaca caataggata aagttctttt ggccacttaa    2220
acaattttct attcttcacc ttttctttt ttctttttt ttttctttg tgggtgtgtg    2280 tgtgtgtgtg tgtgtgtgtg aacactcact gtatttattc cccaattgca tttagttagt    2340
aagaaggagc taagtgttat atttattcat ggaggctata actgttaatt cttccaaatt    2400
gtgaaaaaaa agcctcatag ggtcaataag aacagagtag ttataatcag attgtcacca    2460 aaaagaaaa agaagaaaaa caattaaaca aaacaaacaa acaaaacttt ctagagtgaa    2520
cagtgtcttc taactttctc tcccttcaac ttaagaattc agctcttgag gacataagac    2580
ggtaaatttt atgttatgaa tatgtgatca cagttaaaaa aaaatatgag ggaggttgtt    2640
tttgagtaga cagttgctgg aggaaggcac gtgagttgca gcctgaccag tgcgaccagt    2700
cctccttcaa cagccccgct tgccttgaaa aggcgcccctt actccgctca gggggcctgt    2760
cccgcgcggc tggcacaggc gctcacaata acctcctaaa gcggtgccag ccgcacctcc    2820
gcgcggcccc ggcacaagca gccaatgaac acgcggctgc gcccggcctc gcgcctccat    2880
tggctgcgcc ccgccacccg ctgccccgca ggttcccaag ccgggtttaa aggggtaggg    2940
cgcgggccag ggccccacca tcgtttcccc gcgcgcaggt ccgcggggag gggcggcctg    3000
ccgaccggcc caccccaggg cgttcctgaa gggcgtcctc gg                      3042

<210> SEQ ID NO 2
<211> LENGTH: 1019
<212> TYPE: DNA
<213> ORGANISM: Homo sapiens

<400> SEQUENCE: 2
tgttcaactc ggatagtcct caccactgag ttaatatttc caggtcagag cgcctccgag      60
agaaaaaggc ggtggccttg gagctctggt ctccttaact gcaccctggg aagtcttcac     120
acggcctttc ttcccctggt ggtctaatct ggagtcagat ccagccgtca gctcttacag     180
acggggaagg accgggagcc aacgggaaaa caacaggtga gcttgtgaac aagtccccctt     240 ctgtgtctcg ggcagggtgt ctgcccgggc aaccgtgggg ctgcactgac ttccagaacc     300
ttctgcctct gcaggtgttt taggaacttg gcctcagcgc ttcagtgacc catatttat      360 taccttcag gtttctataa ttcatcattc actcctttct gaaaacctag aatgaaaag      420 tttagcagct cagcgccgcg gcctctctcc attctctccc caaacacatc ggcctgtttg     480
```

| | |
|---|---|
| ttctctttca tccccgctct tcctgttgca ttctgccggt tcaatgggga aggagtgaaa | 540 |
| ccggatggct ggacccagtg cggggaaatg acttcagagc cacctttgtt tccctcattc | 600 |
| ctttgagcgc acttggccct gcgtctctat gaaagggctt gtttgaacca ttcggaacat | 660 |
| ccagcaagcc agagatgctg cggccagaac cgctcgcatc ttttcaggct gcctgagact | 720 |
| ctgggttaaa ctgccaaatt tttgcaacaa aactaaccat gacattggac attgtgttat | 780 |
| aaattagcca cagccttcca agcaaattgt ctcttttat tgtatcagtg taagcctcgg | 840 |
| aaacatttgg cttcagctac taccttcagg gaggctcaga ggatattttt gttctgcccc | 900 |
| aaaccaactc ttcagacacc gagttgcatg tgctaatacc catatcttca ttcacagtta | 960 |
| ttcttatcac actccctctg agaacctctg tcagttatgt tctatttctc tgcctccca | 1019 |

<210> SEQ ID NO 3
<211> LENGTH: 365
<212> TYPE: DNA
<213> ORGANISM: Homo sapiens

<400> SEQUENCE: 3

| | |
|---|---|
| gaaccttcct tgtcctcacg cttgactagc agacaatggg ttcttcagaa gccacagcat | 60 |
| ttcagctgtt ttggccccag aggccacaag ctgactgcat gtcattctcc accagcagag | 120 |
| cgtcacctcg gggtagctcc aaacagtatc aaccggtttg tggtgagtgg ataaacacca | 180 |
| ggctgggtga atgaagtcac aggctgagtc atcctctgca catgggggct gaatggggct | 240 |
| cagtcaggcc cagaggagcc tccccggcaa ggtgctgggg gccaggctct ccctgccagt | 300 |
| gaggctgggg tccgtcccca atagtcattc ctttggccaa caaacactta ttgagcgccc | 360 |
| accta | 365 |

<210> SEQ ID NO 4
<211> LENGTH: 1187
<212> TYPE: DNA
<213> ORGANISM: Homo sapiens

<400> SEQUENCE: 4

| | |
|---|---|
| gctcttcaag tcgcagataa cagtgaaggc cctaagactc accatccaaa acagttttgg | 60 |
| aaaaaaacca agaagagaa ataatttca aaccttaaag caatgcatgg tgattctctg | 120 |
| gggggtctaa gaatttctcc cagagaaatg ataaggcaga caaatggaag atcaatgaag | 180 |
| caacatcgtg gcaataatgc aattggtcct gccgtagtca tgaacatgta aataacaaga | 240 |
| cagcaataag aagaccccag actctgccta gaaacaaaat attcagcctg ttgttgttgt | 300 |
| ttcttattgc aggattttga gtggaaaagt agttccactt gtcaatcagc tacgttgcag | 360 |
| gggctaatag attctggtgt ttagggaggt caacacggaa tttaatttaa catctcacaa | 420 |
| tacacccaca tgcccagaaa atgtggacag cttgataggg ttcactgagc caagaagca | 480 |
| agacccaaac agtgcattaa tgtataggggg aagaatagtt gcaatcagcc ccttgtgaat | 540 |
| tggacagagg gcttggagat gaagcaatta tcagccatcg gggattaata gtaaagtgtg | 600 |
| aataccaagc tgtatatgtt aggggcagaa tatgttgcct atagaaaaca acaaaggacg | 660 |
| tttcttacta ttaagtgaga ttaaacgtaa tggcctgatt taatcacaaa ggcagaatta | 720 |
| aattcagatg gcaacttcaa agtggacaca ggaacacagg ccactgctta catttacata | 780 |
| tagctggcat agcttggcct gcaacacaat aggataaagt ttctttggcc acttaaacaa | 840 |
| ttttctattc ttcaccttt tcttttttc ttttttttt cttttgtggg tgtgtgtgtg | 900 |
| tgtgtgtgtg tgtgtgaaca ctcactgtat ttattcccca attgcattta gttagtaaga | 960 |

```
-continued aggagctaag tgttatattt attcatggag gctataactg ttaattcttc caaattgtga    1020
aaaaaaagcc tcatagggtc aataagaaca gagtagttat aatcagattg tcaccaaaaa    1080
agaaaaagaa gaaaaacaat taaacaaaac aaacaaacaa aactttctag agtgaacagt    1140
gtcttctaac tttctctccc ttcaacttaa gaattcagct cttgagg                  1187

<210> SEQ ID NO 5
<211> LENGTH: 471
<212> TYPE: DNA
<213> ORGANISM: Homo sapiens

<400> SEQUENCE: 5
acataagacg gtaaatttta tgttatgaat atgtgatcac agttaaaaaa aaatatgagg      60
gaggttgttt ttgagtagac agttgctgga ggaaggcacg tgagttgcag cctgaccagt    120
gcgaccagtc ctccttcaac agcccgctt gccttgaaaa ggcgcccta ctccgctcag      180 ggggcctgtc ccgcgcggct ggcacaggcg ctcacaataa cctcctaaag cggtgccagc    240
cgcacctccg cgcggccccg gcacaagcag ccaatgaaca cgcggctgcg cccggcctcg    300
cgcctccatt ggctgcgccc cgccaccgc tgccccgcag gttcccaagc cgggtttaaa    360
ggggtagggc gcgggccagg gccccaccat cgtttccccg cgcgcaggtc cgcggggagg    420
ggcggcctgc cgaccggccc acccccaggg gttcctgaag ggcgtcctcg g             471
```